United States Patent
Shih et al.

(10) Patent No.: US 8,592,287 B2
(45) Date of Patent: Nov. 26, 2013

(54) OVERLAY ALIGNMENT MARK AND METHOD OF DETECTING OVERLAY ALIGNMENT ERROR USING THE MARK

(75) Inventors: Chi-Yuan Shih, Zhubei (TW); I-Hsiung Huang, Hukou Shiang (TW); Heng-Hsin Liu, Yonghe (TW)

(73) Assignee: Taiwan Semiconductor Manufacturing Co., Ltd., Hsin-Chu (TW)

(*) Notice: Subject to any disclaimer, the term of this patent is extended or adjusted under 35 U.S.C. 154(b) by 171 days.

(21) Appl. No.: 13/196,200

(22) Filed: Aug. 2, 2011

(65) Prior Publication Data
US 2013/0032712 A1 Feb. 7, 2013

(51) Int. Cl.
*H01L 21/00* (2006.01)

(52) U.S. Cl.
USPC ............. 438/462; 438/16; 438/401; 438/975; 257/797; 257/E23.179; 356/401

(58) Field of Classification Search
USPC .................... 438/16, 401, 462, 975; 257/797, 257/E23.179; 356/401
See application file for complete search history.

(56) References Cited

U.S. PATENT DOCUMENTS

| | | | |
|---|---|---|---|
| 6,462,818 B1 | 10/2002 | Bareket | |
| 6,486,954 B1 | 11/2002 | Micher et al. | |
| 6,734,971 B2 | 5/2004 | Smith et al. | |
| 7,379,184 B2 | 5/2008 | Smith et al. | |
| 2004/0004726 A1 | 1/2004 | Sezginer et al. | |
| 2005/0012928 A1* | 1/2005 | Sezginer et al. | 356/401 |
| 2006/0197950 A1 | 9/2006 | Smith et al. | |
| 2007/0018099 A1* | 1/2007 | Chitturi et al. | 250/310 |
| 2012/0183676 A1* | 7/2012 | Sonoda et al. | 427/8 |

* cited by examiner

*Primary Examiner* — Kimberly Rizkallah
*Assistant Examiner* — Maria Ligai
(74) *Attorney, Agent, or Firm* — Duane Morris LLP; Steven E. Koffs

(57) ABSTRACT

A method comprises providing a semiconductor substrate having a first layer and a second layer above the first layer. The first layer haw a plurality of first patterns, vias or contacts. The second layer has second patterns corresponding to the first patterns, vias or contacts. The second patterns have a plurality of in-plane offsets relative to the corresponding first patterns, vias or contacts. A scanning electron microscope is used to measure line edge roughness (LER) values of the second patterns. An overlay error is calculated between the first and second layers based on the measured LER values.

13 Claims, 14 Drawing Sheets

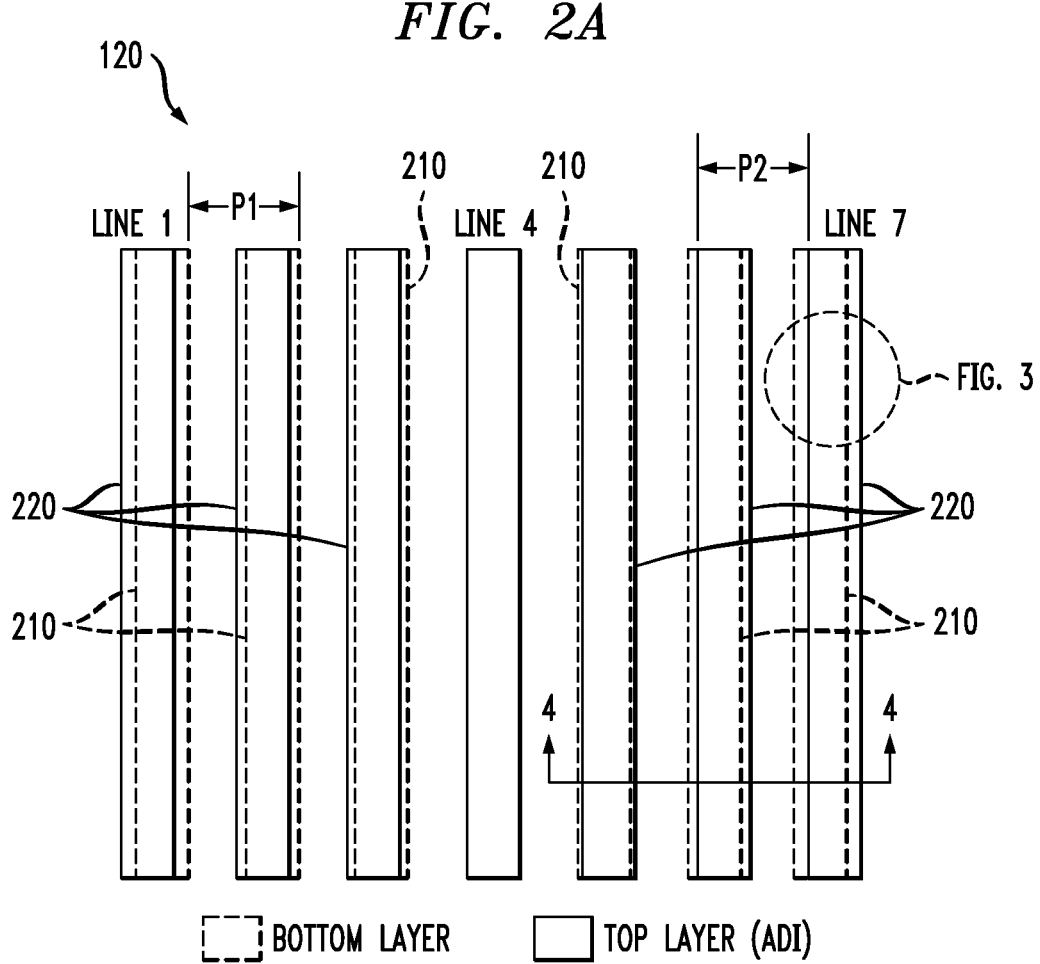

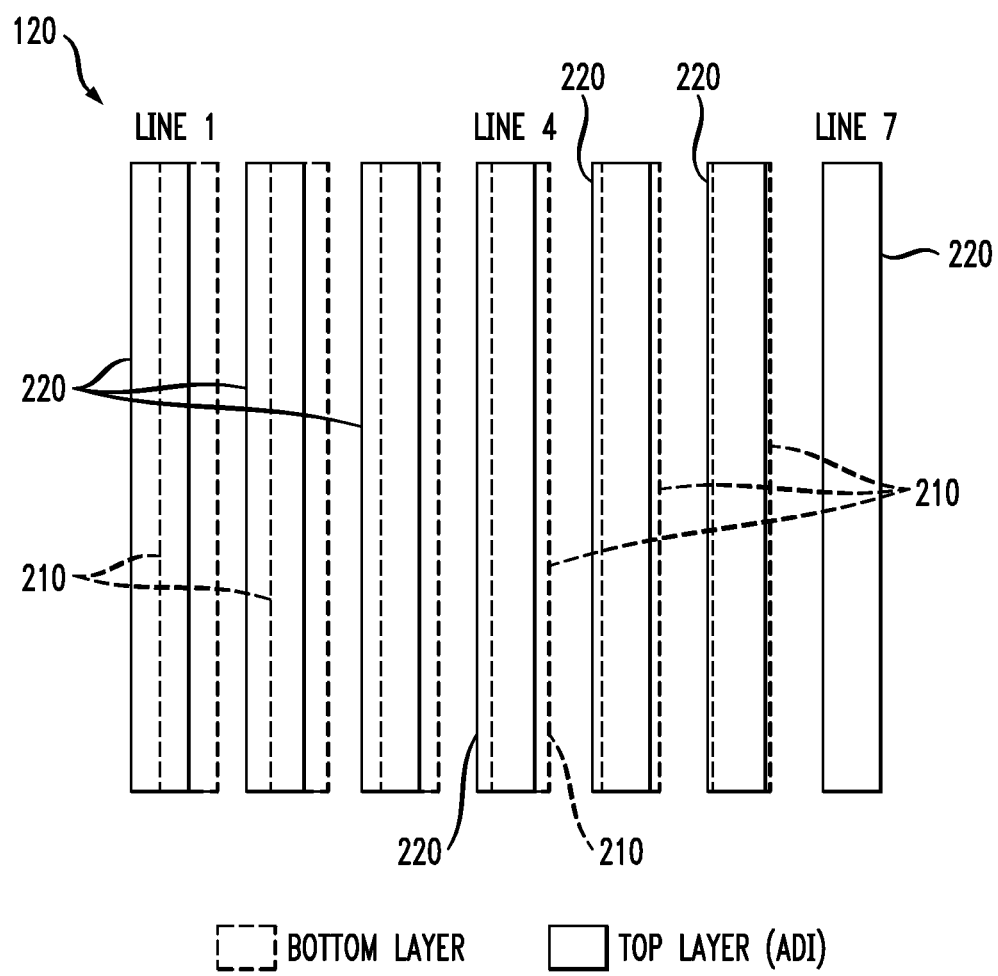

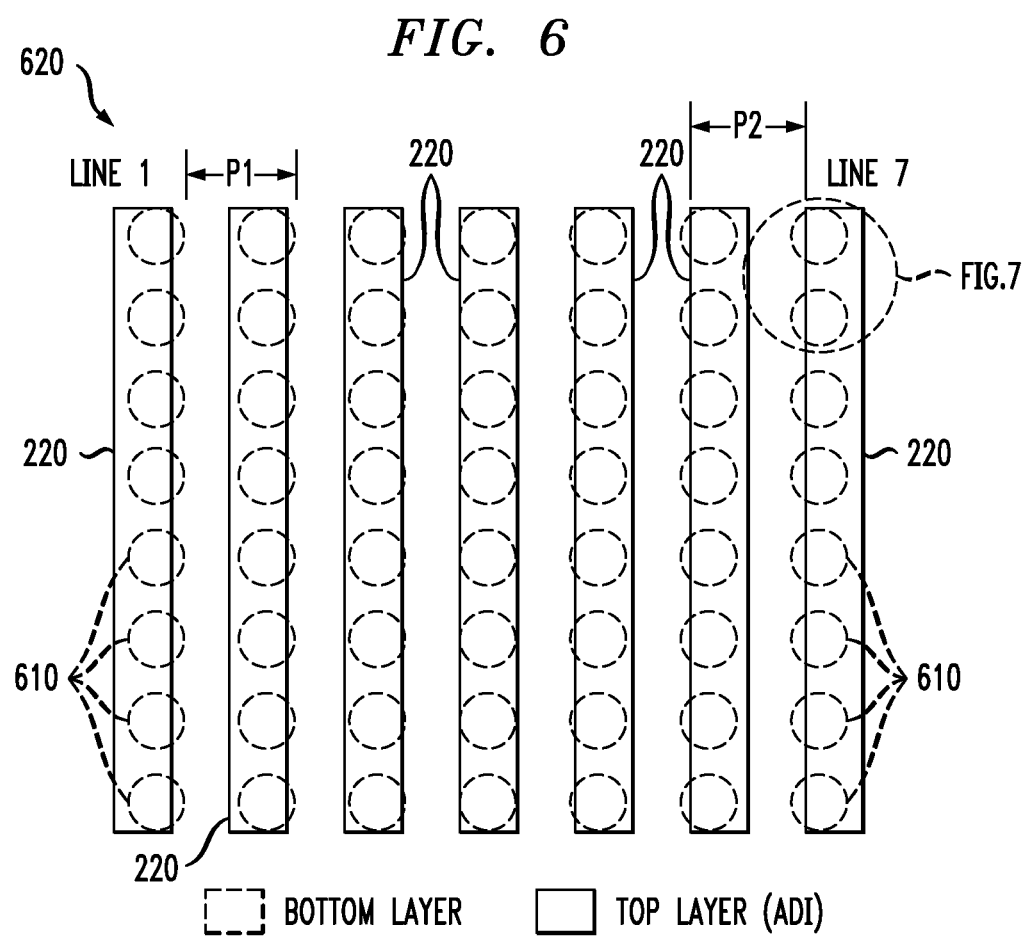

OVERLAY ALIGNMENT MARK AND METHOD OF DETECTING OVERLAY ALIGNMENT ERROR USING THE MARK

FIELD

This disclosure relates to measurement of overlay alignment errors between plural patterned layers in semiconductor integrated circuits (ICs).

BACKGROUND

During semiconductor IC fabrication, 20 or more layers of material are successively deposited and patterned over a semiconductor substrate. Good function, performance and yield requires that the various layers be well aligned with each other. Additionally, with the advent of double patterning techniques, it is also important to be able to detect alignment errors between patterns formed by plural exposures on the same layer.

In order to detect and measure alignment errors, alignment marks are commonly placed in the scribe lines on the wafer. Several alignment marks are included, so that an average alignment error across the wafer can be determined. A variety of alignment mark shapes and sizes have been used. Generally, a first portion of the pattern is located on a first (lower) layer and a second portion of the pattern is located on a second (upper layer) above the first layer. The pattern portions are typically configured so that, when alignment is correct, the upper portion either directly overlies the lower portion, or a known spatial relationship is present between the upper and lower portion. Any deviation between the actual spatial relationship of the pattern portions and the expected relationship can be measured optically to determine the size of the alignment error.

As a general rule of thumb, alignment errors are maintained at less than 20% of the smallest dimension of any element of any of the patterns. As device sizes are reduced with each new technology node, the size of the allowable alignment error is correspondingly reduced. Improved overlay alignment error measurement methods and systems are desired.

BRIEF DESCRIPTION OF THE DRAWINGS

FIG. 2A is a schematic diagram of an embodiment of the alignment mark of FIG. 1.

FIG. 2B show the alignment mark of FIG. 2A, with an overlay alignment error present.

FIG. 6 is a schematic diagram of a second embodiment of the alignment mark of FIG. 1.

DETAILED DESCRIPTION

Figure 1:
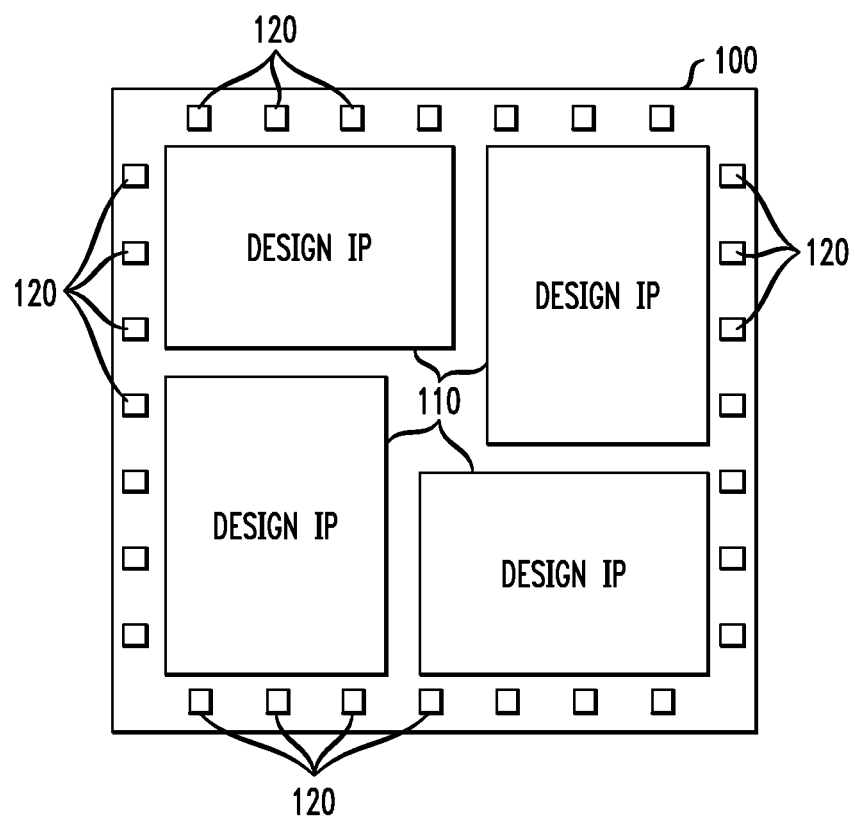
FIG. 1 is a schematic diagram of an IC chip having a plurality of overlay alignment marks within the chip area.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

In various embodiments, measurements of an alignment mark are collected using a scanning electron microscope (SEM). Overlay alignment errors may be calculated, based on a line edge roughness of measured lines within the alignment mark, or circularity of measured holes within the alignment mark. An alignment mark suitable for measurement by SEM may be formed with a reduced size, for example 2 µm×2 µm. An alignment mark of this size may optionally be included within the chip area, without increasing chip size. Thus, alignment marks may be included in wafers having reduced scribe line width, or no scribe lines. The alignment mark may have a first portion formed in a metal or via layer, and a second portion formed in a photoresist layer. Thus, the method enables overlay alignment checking during after-develop-inspection (ADI), before etching.

FIG. 1 is a schematic diagram of an IC die 100 having a plurality of alignment marks 120 within the layout area of the die. Local variation of LER and circularity may be compensated with local LER and circularity averaging from repeating alignment marks 120. The die 100 has a plurality of design IP circuits 110, which perform the operational functions of the die. Although FIG. 1 only shows alignment marks 120 around the perimeter of the die, in other embodiments, one or more of the alignment marks may be located in the interior of the die, for example, between the design IP circuits 110. The number of alignment marks may be varied.

FIG. 2A is an enlarged diagram of one of the overlay alignment marks 120 of FIG. 1. A first layer above a semiconductor substrate has a plurality of first features 210 from the group consisting of first lines, first rows of vias and first rows of contacts. In the example of FIG. 2A, the first features are lines 210, shown in phantom. The dashed lines in features 210 indicate that the lines are in a lower (hidden) layer, but the lines 210 may be solid lines. Adjacent ones of the first features 210 are separated from each other by a first pitch P1.

A second layer is provided above the first layer. The second layer has second features 220 corresponding to the first lines or first rows. For each line 210, there is a corresponding second feature 220. The second features are selected from the group consisting of second lines and second rows of holes. In the example of FIG. 2A, the second features are lines. Adjacent ones of the second features 220 are separated by a second pitch P2 that is different from the first pitch, such that the second features 220 have a plurality of in-plane offsets relative to the corresponding first features 210.

The overlay is the distance between the center of the upper (second) line 220 to the center of the lower (first) line 210. So when the overlay is zero, the lines are directly over each other. In FIG. 2A, the fourth pattern (of seven), which is the center pattern, has an overlay of zero, so that the center upper pattern 220 directly overlies the center lower pattern 210. In FIG. 2A, absent an alignment error, the overlay of the center patterns is zero. For the remaining pairs of lower lines 210 and upper lines 220, the offset (overlay) between the lower and upper line increases with distance from the center line.

Figure 4:
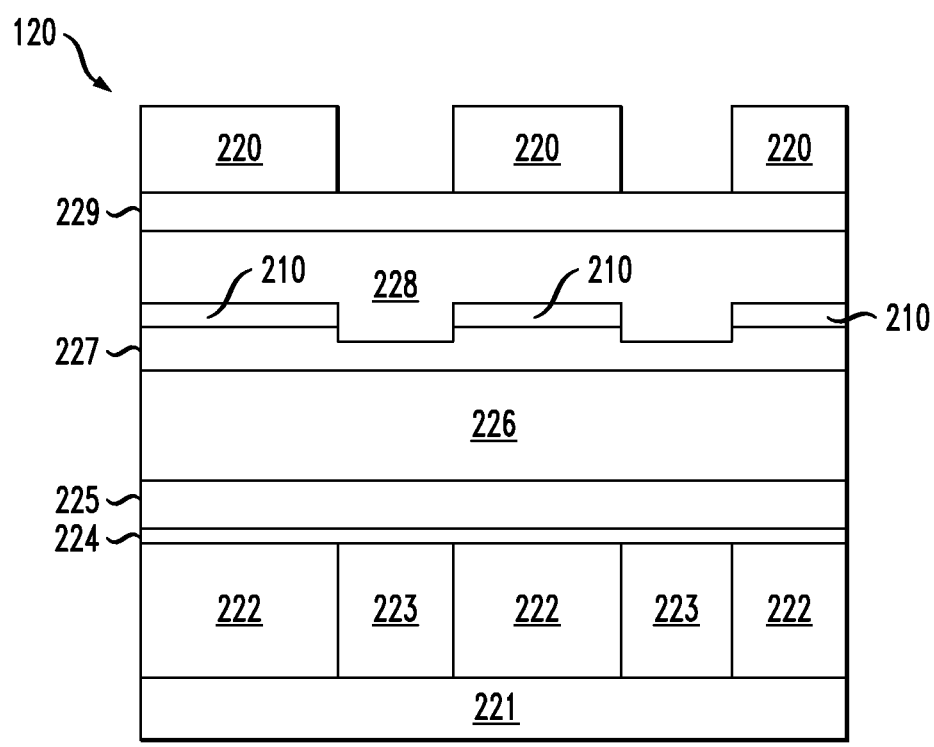
FIG. 4 is a cross sectional view taken along section line 4-4 of FIG. 2A.

FIG. 4 is a cross sectional view taken along line 4-4 of FIG. 2A. In FIG. 4, the first layer 210 and the second layer 220 are shown within a stack of layers. In this example, the first layer having patterns 210 is a metal hard mask (MHM) layer, and may be the M2 layer of the back end of line (BEOL) interconnect structure. The second layer having patterns 220 is a V1 photoresist layer (used for the V1 via layer of the interconnect structure). The center pattern 220 is directly over its corresponding pattern 210, absent overlay alignment errors. The other layers shown in FIG. 4 include interlevel dielectric (ILD) 221, M1 extreme low-k (ELK) 222, M1 copper (M1 Cu) 223, M2 SiC 224, tetra-ethoxy-silane (TEOS) 225, M2 extreme low-k (M2 ELK) 226, M2 etch stop layer (M2 ESL) 227, V1 barrier layer (V1 BL), and V1 ML 229. FIG. 4 is just one example, and the method may be applied in any stack of layers over a substrate.

Figure 3:
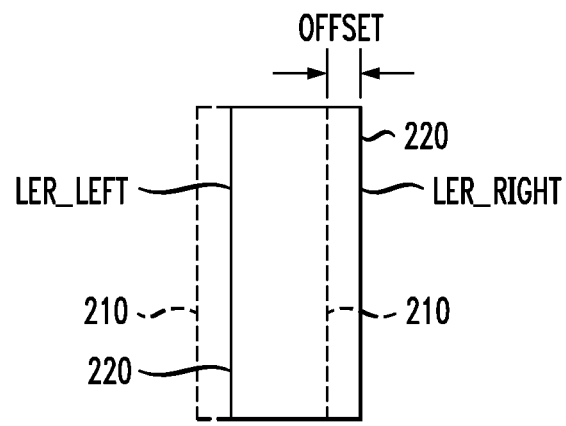
FIG. 3 is an enlarged detail of FIG. 2A

FIG. 3 is an enlarged detail of FIG. 2A, showing one of the pairs including a lower line 210 and upper line 220. In some embodiments, the first features 210 are conductive patterns formed in an interconnect layer, and the second features are formed in a photoresist layer. For example, the first features 210 may be conductive lines formed of copper. The left edge of the upper line 220 overlies the lower (copper) line 210, but the right edge of the upper line 220 overlies dielectric material. The difference between materials underlying the left and right edges has a differential effect on the line edge roughness (LER) of the upper lines 220. SEM measurements provide the LER of each of the edges of the upper lines 220. Note that only the upper lines 220 are measured by the SEM.

The inventors have determined that the ADI Line Edge Roughness (LER) is a function of bottom layer topography and reflectivity. The asymmetry of LER on the two edges of the upper lines 220 can be used to pin-point the overlay value (due to different topography and photo reflectivity on two edges). The difference between the LER of the left edge and the LER of the right edge of lines 220 varies with the amount of overlay (the offset between the upper patterns 220 and lower patterns 210). When the upper pattern 220 directly overlies the lower pattern 210 (zero overlay), the LER_LEFT and LER_RIGHT measurements are very close to each other, and show a high "LER correlation."

Figure 5A:
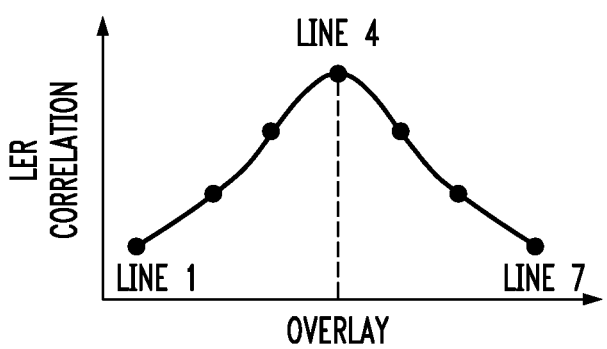
FIG. 5A is a diagram of the line edge roughness (LER) correlation in the various patterns shown in FIG. 2A.

FIG. 5A is a diagram showing the LER correlation (inverse of the difference between LER_LEFT and LER_RIGHT) plotted for the various lines in the mark of FIG. 2A. When the upper features 220 are properly aligned with the lower features 210, as shown in FIG. 2A, a predetermined upper line 220 has zero overlay, and directly overlies its corresponding lower line 210 (In FIG. 2A, the fourth line 220 directly overlies the fourth line 210). The overlay (offset between the upper and lower line) increases in both directions, with distance from the center line. As a result, the inverse of the difference between LER_LEFT and LER_RIGHT for this correctly aligned mark, as shown in FIG. 5A, has its maximum value for the fourth lines 210, 220.

Figure 5B:
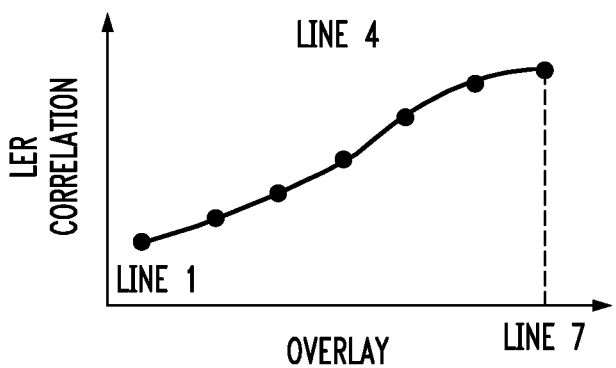
FIG. 5B shows the inverse of the difference between LER_LEFT and LER_RIGHT for the alignment mark of FIG. 2A.

FIG. 2B shows the same alignment mark as it would appear if the upper and lower layers are not correctly aligned. In the example of FIG. 2B, the rightmost lines 210, 220 (the seventh pair of lines) are directly aligned with each other, and all the remaining pairs of lines have various offsets, increasing with distance from the seventh pair of lines 210, 220. FIG. 5B shows the inverse of the difference between LER_LEFT and LER_RIGHT for the alignment mark of FIG. 2A. Rather than the fourth pair of lines having the maximum LER correlation, the seventh pair of lines has the maximum value. This indicates that the upper layer is offset from the lower layer by three times the difference between the pitches P1 and P2. Similarly, if there are intermediate amounts of offset, line 5 or line 6 may show the highest LER correlation, indicating an alignment error of one or two times the difference in pitches, respectively.

Thus, by determining which of the patterns 220 has the greatest LER correlation (i.e., the smallest difference between LER_LEFT and LER_RIGHT), the overlay alignment error can be measured with fine precision. For a 1 um×1 um alignment mark of FIG. 2A with 7 lines, what is the metrology precision of the alignment mark is dominated by the SEM precision, and should be less than 1 nanometer.

Although in FIG. 2A, the center line 220 is the predetermined line that directly overlies its corresponding line 210 if there is no overlay alignment error, in other embodiments, a different pair of lines (e.g., the third pair or fifth pair, on either side next to the center pair) may have zero overlay when there is no alignment error. For example, if alignment errors are biased to one side of the center, then the alignment mark may be configured to provide more patterns on one side of the directly aligned pair of lines than on the other.

Although the example include seven pairs of patterns, any number of patterns may be used. Odd numbers of patterns (e.g., 5, 7 or 9) provide a center pattern, which allows a symmetric arrangement with a single zero overlay line pair.

Figure 7:
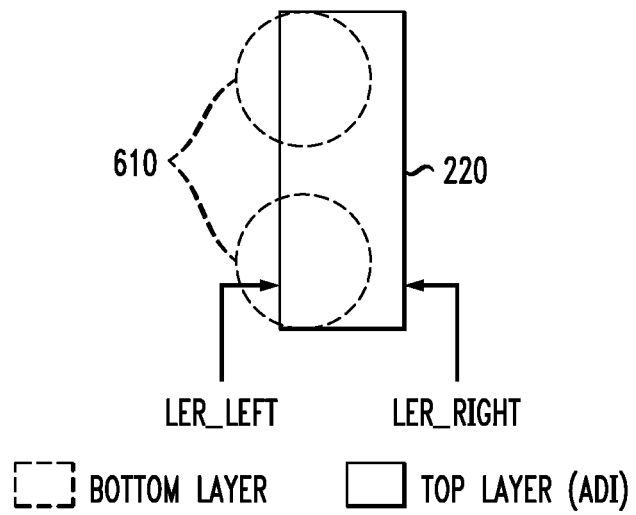
FIG. 7 is an enlarged detail of FIG. 6
Figure 8:
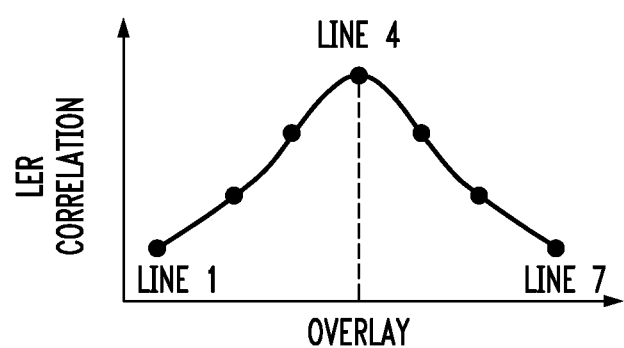
FIG. 8 is a diagram of the line edge roughness (LER) correlation in the various patterns shown in FIG. 6.

A variety of overlay alignment marks may be used. For example, the lower layer features need not be lines. FIGS. 6 and 7 show a variation of the alignment mark 620, in which the features 610 in the lower layer are rows (or columns) of vias or contacts, which may be formed of copper or aluminum, for example. The rows or columns extend parallel to the lines 220 in the upper layer. The vias/contacts 610 may be round, as shown, or rectangular (not shown). Each row (or column) of vias or contacts 610 works similarly to the lines 210 of FIG. 2A. An alignment error between one of the rows of vias/contacts 610 and the corresponding upper line 220 causes a measurable difference between the LER of the right and left edges of the overlying line 220. The difference increases with the amount of offset between the vias/contacts 610 and the lines 220. Thus, the LER correlation may be plotted, as shown in FIG. 8, to determine which of the patterns 220 is most closely aligned with its underlying row of vias/contacts 220. The upper layer may be a photoresist layer, and the upper layer features may be photoresist lines 220, of the same type shown in FIGS. 2A and 2B.

Figure 9:
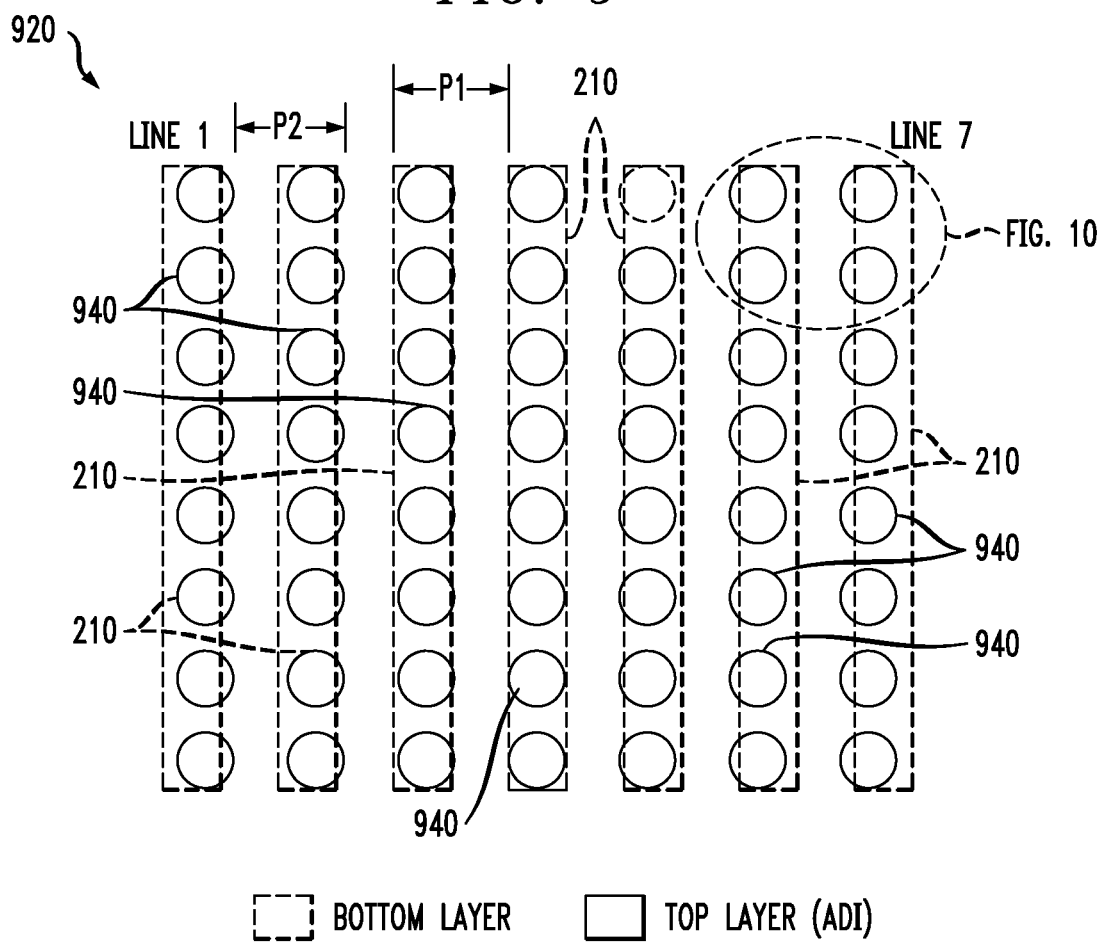
FIG. 9 is a schematic diagram of a third embodiment of the alignment mark of FIG. 1.
Figure 10:
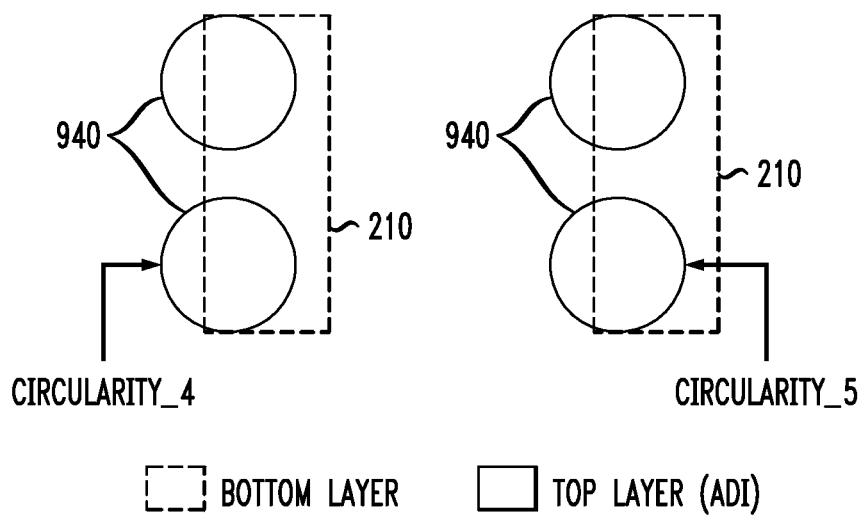
FIG. 10 is an enlarged detail of FIG. 9

FIGS. 9 and 10 show a variation of the alignment mark, in which the lower layer features may be lines 210, as shown in FIG. 2A, but the upper layer features are rows (or columns) of holes 940, where the rows or columns are parallel to the lines 210 below. The pitch between adjacent rows of holes is different from the pitch between adjacent pairs of the underlying lines. The inventors have determined that an alignment error between one of the lines 210 and the row of holes 940 above the line causes a reduction in the circularity of the hole 940. For a perfectly aligned hole (with zero overlay), the circularity is substantially 1.0. The size of the reduction in circularity varies with the size of the alignment error. Thus, for the patterns 210, 940 shown in FIG. 10, the right holes 940 have lower circularity than the left holes, indicating that the right holes are offset from their underlying line 210 more than the left holes. The center (fourth) column of holes 210 directly overlies its corresponding line, and has circularity of substantially 1.0.

Figure 11:
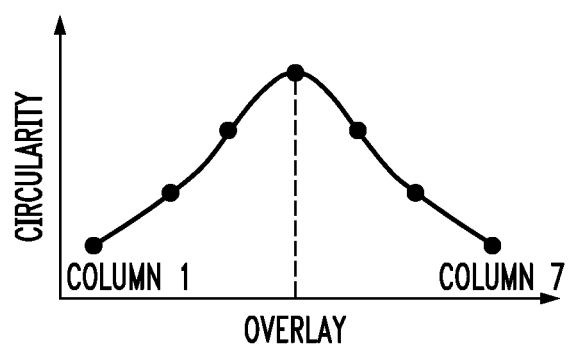
FIG. 11 is a diagram of the circularity in the various holes shown in FIG. 9.

FIG. 11 is a plot of the circularity of the holes 940 plotted against the location of the row of holes within the alignment mark. As in the case of the alignment mark of FIG. 2A, when the layers are correctly aligned, the maximum circularity occurs at the predetermined (e.g., center) row of holes. If the maximum circularity is found at any other row of holes 940, the size of the overlay alignment error can be determined by determining the row of holes 940 having maximum circularity.

Although the above described examples include straight, solid lines, other types of lines may be used. In other embodiments, different line formats are used to stimulate the differences in LER between line edges overlying metal and line edges overlying dielectric (or to stimulate differences between circularity of aligned holes and circularity of offset holes.

Figure 12:
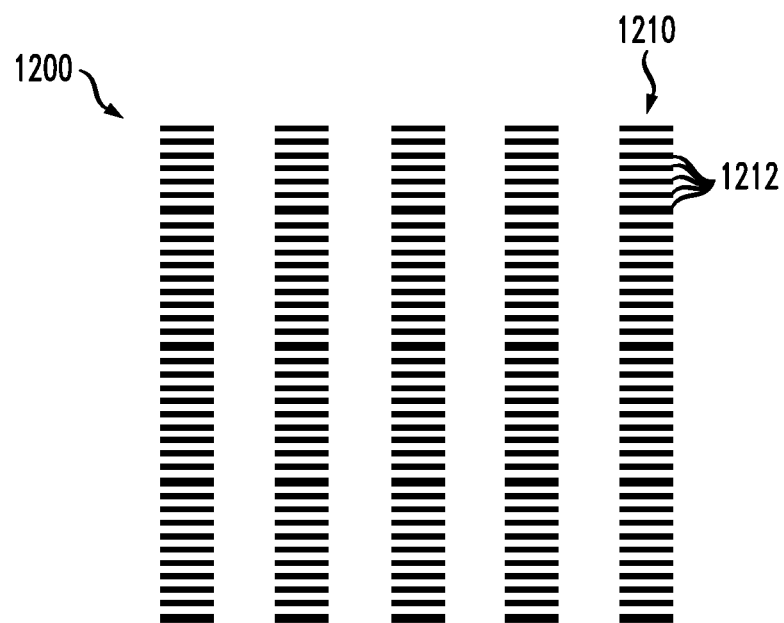
FIG. 12 is a diagram of segmented lines that may be used in the second (upper) layer of the alignment mark of FIG. 2 or 6 or the first (lower) layer of the marks of FIG. 2 or 9.

FIG. 12 shows an alternative line format that may be used in either the first (lower) features or the second (upper) features are undulating lines. In the alignment mark 1200 of FIG. 12, either the underlying conductive lines or the upper photoresist lines may be segmented. Each line 1210 comprises a plurality of parallel line segments 1212. The segments 1212 run perpendicular to the length direction of the lines 1210.

Figure 13:
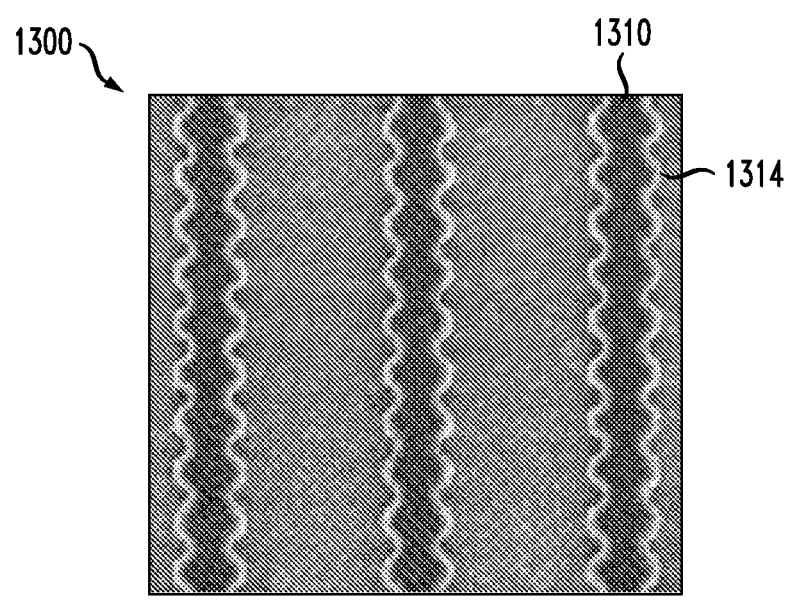
FIG. 13 is a diagram of lines having undulating (serpentine) edges, which may be used in the second (upper) layer of the alignment mark of FIG. 2 or 6 or the first (lower) layer of the mark of FIG. 2 or 9.

FIG. 13 is a diagram of another line format which may be used for the lower features 210 or the upper features 220. In FIG. 13, the patterns are lines with undulating (serpentine) edges.

Figure 14:
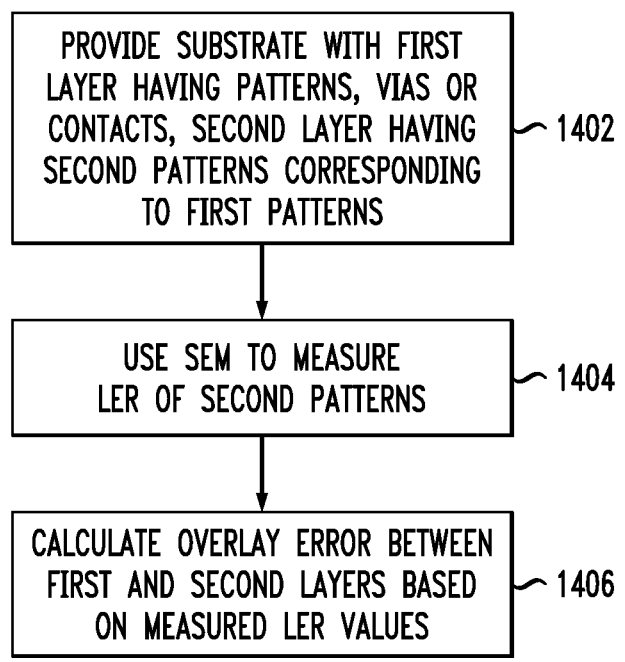
FIG. 14 is a flow chart of a method of measuring an overlay error using the alignment marks of FIG. 2A or 6.

FIG. 14 is a flow chart of a method of using the overlay alignment marks of FIG. 2A, 2B or 6.

At step 1402, a semiconductor substrate is provided. The substrate has a first layer and a second layer above the first layer. The first layer has a plurality of first patterns, vias or contacts. The first patterns are lines separated by a first pitch. The second layer has second patterns corresponding to the first patterns, vias or contacts. The second patterns are lines separated by a second pitch that is different from the first pitch. The second patterns have a plurality of in-plane offsets relative to the corresponding first patterns, vias or contacts. Optionally, the first and second patterns form alignment marks within the layout area of the integrated circuit.

At step 1404, a scanning electron microscope (SEM) is used to measure line edge roughness (LER) values of the second patterns.

At step 1406, an overlay error between the first and second layers is calculated, based on the measured LER values.

Figure 15:
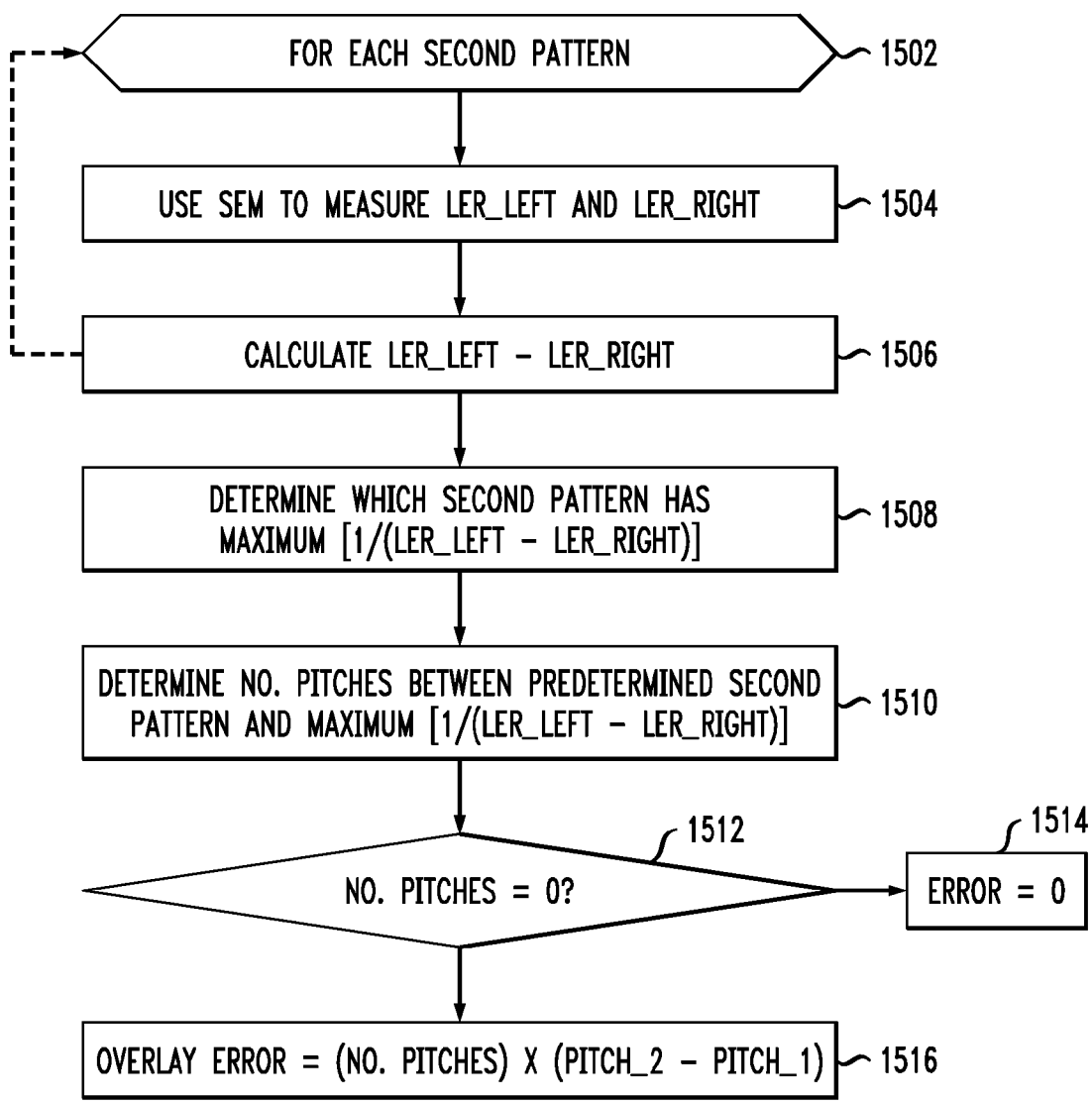
FIG. 15 is a detailed flow chart of the measurement and calculation in FIG. 14.

FIG. 15 is a more detailed flow chart of the measuring and analysis steps.

At step 1502, a loop including steps 1504 and 1506 is performed for each of the patterns of the second (upper) layer.

At step 1504, an SEM is used to measure line edge roughness (LER) values of the second patterns.

At step 1506, the difference between the LER of the left and right edges is calculated. For each second pattern, the LER of the second edge is subtracted from the LER of the first edge to calculate a respective difference for that second pattern.

At step 1508, a determination is made as to which one of the second patterns has the greatest LER correlation (i.e., the smallest difference among the second patterns of the overlay alignment mark). The LER correlation is given by [1/(LER_LEFT-LER_RIGHT)]

At step 1510 the number of pitches between the predetermined second pattern (for which the second pattern directly overlies the first pattern in the absence of overlay alignment error) and the pattern having the greatest LER correlation is determined. For example, if the alignment mark of FIG. 2A is used, the number of pitches between the center pattern (fourth line) and the pattern having greatest LER correlation is determined.

At step 1512, the process determines whether the predetermined one of the second patterns (e.g., the center line) has the greatest LER correlation (i.e., smallest difference). If the predetermined pattern has the greatest LER correlation, step 1514 is executed. Otherwise, step 1516 is executed.

At step 1514, the overlay alignment error is zero

At step 1516, if another one of the second patterns (besides the predetermined or center line) has the smallest difference, the overlay error is calculated as a product of (a number of second pitches between the predetermined second pattern and the other second pattern)×(a difference between the first pitch and the second pitch).

Figure 16:
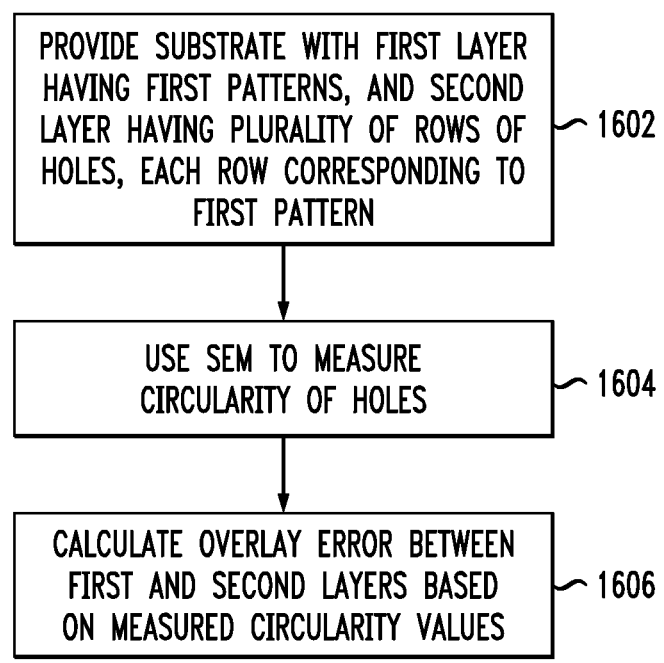
FIG. 16 is a flow chart of a method of measuring an overlay error using the alignment mark of FIG. 9.

FIG. 16 is a high level flow chart of another exemplary method using an overlay alignment mark of the type shown in FIG. 9.

At step 1602, a semiconductor structure is provided having a first layer and a second layer above the first layer. The first layer has a plurality of first patterns. The second layer has a plurality of rows of holes. Each row of holes corresponds to a respective one of the first patterns. The plurality of rows have a plurality of in-plane offsets relative to the corresponding first patterns.

At step 1602, a scanning electron microscope is used to measure circularity values of the holes in each row of holes.

At step 1604, an overlay error between the first and second layers is calculated based on the measured circularity values.

Figure 17:
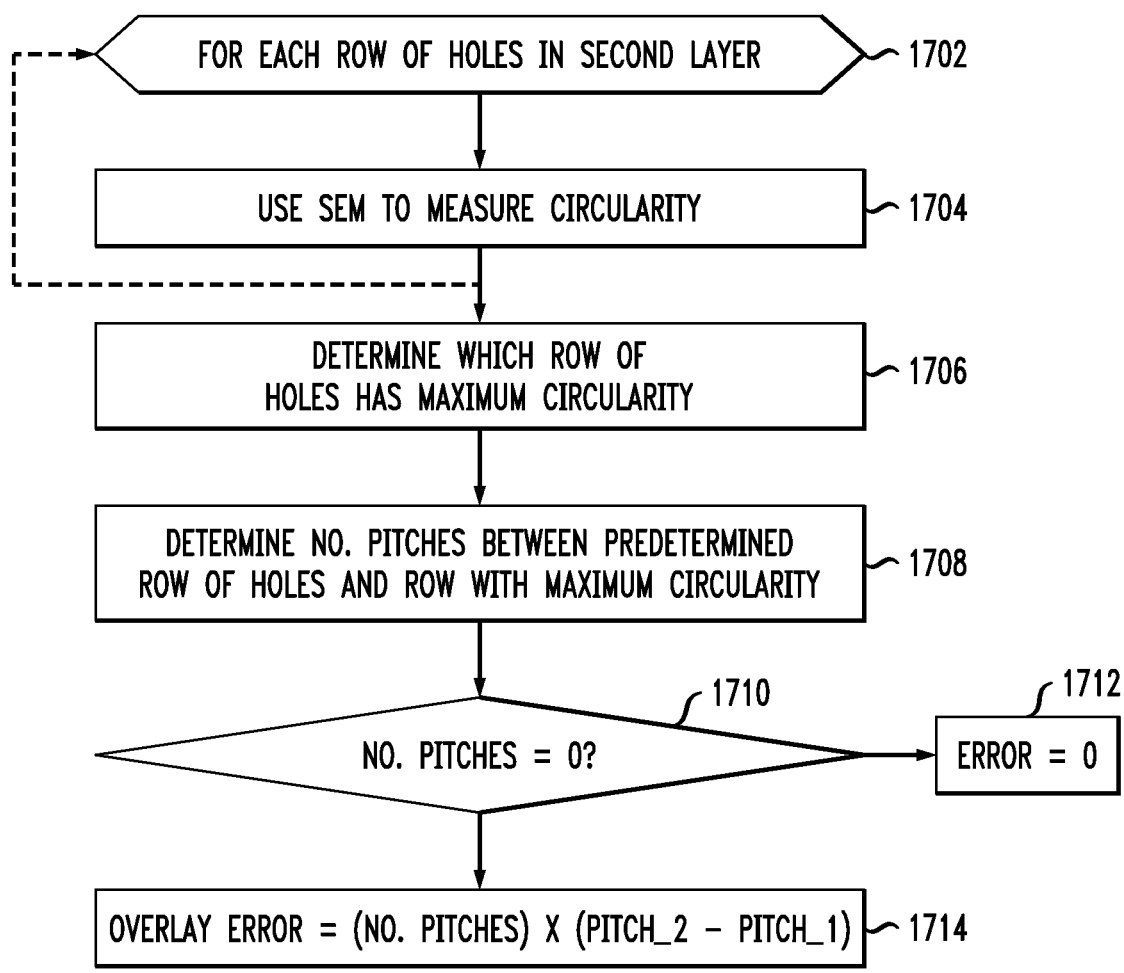
FIG. 17 is a detailed flow chart of the measurement and calculation in FIG. 16.

FIG. 17 is a detailed flow diagram of the measuring and analysis steps of FIG. 16.

At step 1702, step 1704 is repeated for each row of holes in the second layer.

At step 1704, an SEM is used to measure the circularity of each hole in the second layer. For each respective row, the respective average circularity is determined, for example, using the arithmetic mean of all the holes in that row.

At step 1706, a determination is made which one of the rows of holes has a largest average circularity among the plurality of rows of holes of the overlay alignment mark.

At step 1708, the number of pitches between the predetermined second pattern (for which the row of holes directly overlies the first pattern in the absence of overlay alignment error) and the row having the greatest measured average circularity is determined. For example, if the alignment mark of FIG. 9 is used, the number of pitches between the center pattern (fourth row of holes) and the pattern having greatest circularity is determined.

At step 1710, the process determines whether the predetermined one of the second patterns (e.g., the center row) has the greatest circularity. If the predetermined pattern has the greatest circularity, step 1712 is executed. Otherwise, step 1714 is executed.

At step 1712, the overlay error is zero

At step 1714, if another one of the second patterns (besides the predetermined or center row of holes) has the greatest circularity, the overlay error is calculated as a product of (a number of second pitches between the predetermined second pattern and the other second pattern)×(a difference between the first pitch and the second pitch).

Many variations are within the scope of the disclosure. For example, the resolution of overlay error calculation from SEM measurement data of LER or circularity asymmetry can be enhanced with a curve-fitting technique. The curve fitting is implemented to the LER or circularity correlation data points with parabolic or other polynomial equations. The overlay error can then be extracted from the peak position of the curve. This is one example showing that the overlay error resolution is not limited to the pitch difference of top/bottom layers.

In some embodiments, a method comprises providing a semiconductor substrate having a first layer and a second layer above the first layer. The first layer haw a plurality of first patterns, vias or contacts. The second layer has second patterns corresponding to the first patterns, vias or contacts. The second patterns have a plurality of in-plane offsets relative to the corresponding first patterns, vias or contacts. A scanning electron microscope is used to measure line edge roughness (LER) values of the second patterns. An overlay error is calculated between the first and second layers based on the measured LER values.

In some embodiments, a method comprises providing a semiconductor structure having a first layer and a second layer above the first layer. The first layer has a plurality of first patterns. The second layer has a plurality of rows of holes, each row of holes corresponding to a respective one of the first patterns. The plurality of rows have a plurality of in-plane offsets relative to the corresponding first patterns. A scanning electron microscope is used to measure circularity values of the holes in each row of holes. An overlay error between the first and second layers is calculated based on the measured circularity values.

In some embodiments, an overlay alignment mark structure comprises a first layer above a semiconductor substrate, the first layer having a plurality of first features from the group consisting of first lines, first rows of vias and first rows of contacts. Adjacent ones of the first features are separated from each other by a first pitch. A second layer is provided above the first layer. The second layer has second features corresponding to the first lines or first rows. The second features are selected from the group consisting of second lines and second rows of holes. Adjacent ones of the second features are separated by a second pitch that is different from the first pitch, such that the second features have a plurality of in-plane offsets relative to the corresponding first features.

The methods described herein may be at least partially embodied in the form of computer-implemented processes and apparatus for practicing those processes. The disclosed methods may also be at least partially embodied in the form of tangible, non-transient machine readable storage media encoded with computer program code. The media may include, for example, RAMs, ROMs, CD-ROMs, DVD-ROMs, BD-ROMs, hard disk drives, flash memories, or any other non-transient machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, when the computer program code is loaded into and executed by a computer, the computer becomes an apparatus for practicing the methods. When implemented on a general-purpose processor, the computer program code segments configure the processor to create specific logic circuits. The methods may alternatively be at least partially embodied in a digital signal processor formed of application specific integrated circuits for performing the methods.

Although the subject matter has been described in terms of exemplary embodiments, it is not limited thereto. Rather, the appended claims should be construed broadly, to include other variants and embodiments, which may be made by those skilled in the art.

What is claimed is:

1. A method comprising:
   providing a semiconductor substrate having a first layer and a second layer above the first layer, the first layer having a plurality of first patterns, vias or contacts, the second layer having second patterns corresponding to the first patterns, vias or contacts, the second patterns having a plurality of in-plane offsets relative to the corresponding first patterns, vias or contacts;
   using a scanning electron microscope to measure line edge roughness (LER) values of the second patterns; and
   calculating an overlay error between the first and second layers based on the measured LER values.

2. The method of claim 1, wherein:
   the first patterns are lines separated by a first pitch; and
   the second patterns are lines separated by a second pitch that is different from the first pitch.

3. The method of claim 2, wherein the second patterns are lines with undulating edges.

4. The method of claim 2, wherein the second patterns are segmented lines, each segmented line comprising a plurality of parallel line segments.

5. The method of claim 1, wherein
   the first and second patterns form an overlay alignment mark;
   each second pattern has a first edge and a second edge; and
   the calculating step includes, for each second pattern, subtracting the LER of the second edge from the LER of the first edge to calculate a respective difference for that second pattern, wherein the overlay error is determined based on which one of the second patterns has a smallest difference among the second patterns of the overlay alignment mark.

6. The method of claim 5 wherein
   the first patterns are lines or rows of vias or contacts separated by a first pitch;
   the second patterns are lines separated by a second pitch;
   if a predetermined one of the second patterns has the smallest difference, then the overlay error is zero; and
   if another one of the second patterns has the smallest difference, the overlay error is calculated as a product of (a number of second pitches between the predetermined second pattern and the other second pattern)×(a difference between the first pitch and the second pitch).

7. The method of claim 1, wherein:
   each of the first patterns includes a respective row of vias or contacts, adjacent ones of the rows separated by a first pitch; and
   the second patterns are lines separated by a second pitch that is different from the first pitch.

8. The method of claim 1, wherein:
the first patterns are conductive patterns in an interconnect layer,
the second layer is a photoresist layer, and
the step of using the scanning electron microscope is performed after developing the photoresist, and before performing a next etching step.

9. The method of claim 1, wherein
the first and second patterns form a plurality of overlay alignment marks; and
the providing step includes providing the plurality of overlay alignment marks within a layout area of an integrated circuit die.

10. A method comprising:
providing a semiconductor structure having a first layer and a second layer above the first layer, the first layer having a plurality of first patterns, the second layer having a plurality of rows of holes, each row of holes corresponding to a respective one of the first patterns, the plurality of rows having a plurality of in-plane offsets relative to the corresponding first patterns;
using a scanning electron microscope to measure circularity values of the holes in each row of holes; and
calculating an overlay error between the first and second layers based on the measured circularity values.

11. The method of claim 10, wherein:
the first patterns are lines separated by a first pitch; and
the rows of holes are separated from each other by a second pitch that is different from the first pitch.

12. The method of claim 10, wherein
the first and second patterns form an overlay alignment mark;
the calculating step includes determining which one of the rows of holes has a largest average circularity among the plurality of rows of holes of the overlay alignment mark.

13. The method of claim 12 wherein
the first patterns are lines or rows of vias or contacts separated by a first pitch;
the rows of holes are separated by a second pitch different from the first pitch;
if a predetermined one of the rows of holes has the largest average circularity, then the overlay error is zero; and
if another one of the rows of holes has the largest average circularity, the overlay error is calculated as a product of (a number of second pitches between the predetermined rows of holes and the other rows of holes)×(a difference between the first pitch and the second pitch).

* * * * *